(12) United States Patent
Kirby et al.

(10) Patent No.: US 10,138,740 B2
(45) Date of Patent: Nov. 27, 2018

(54) SILICON-BASED MATERIALS CONTAINING GALLIUM AND METHODS OF FORMING THE SAME

(71) Applicant: General Electric Company, Schenectady, NY (US)

(72) Inventors: Glen Harold Kirby, Liberty Township, OH (US); Julin Wan, Rexford, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/267,335

(22) Filed: Sep. 16, 2016

(65) Prior Publication Data

US 2018/0080331 A1   Mar. 22, 2018

(51) Int. Cl.
| | |
|---|---|
| *B32B 15/04* | (2006.01) |
| *F01D 5/28* | (2006.01) |
| *C04B 35/16* | (2006.01) |
| *C04B 35/50* | (2006.01) |
| *C04B 35/48* | (2006.01) |
| *C04B 35/584* | (2006.01) |

(Continued)

(52) U.S. Cl.
CPC ............. *F01D 5/288* (2013.01); *C01G 15/00* (2013.01); *C04B 35/16* (2013.01); *C04B 35/48* (2013.01); *C04B 35/50* (2013.01); *C04B 35/565* (2013.01); *C04B 35/58* (2013.01); *C04B 35/584* (2013.01); *C30B 29/406* (2013.01); *C07C 2523/08* (2013.01); *C07C 2523/825* (2013.01); *F05D 2300/502* (2013.01); *F05D 2300/6033* (2013.01); *F05D 2300/611* (2013.01)

(58) Field of Classification Search
CPC ................ C01G 15/00; C07C 2523/08; C07C 2523/825; C30B 29/406; C04B 35/16; C04B 35/48; C04B 35/50; C04B 35/565; C04B 35/58; C04B 35/584; F05D 2300/502; F05D 2300/6033; F05D 2300/611; F01D 5/288
See application file for complete search history.

(56) References Cited

U.S. PATENT DOCUMENTS 6,644,917 B2 * 11/2003 Zhao ...................... C23C 30/00
                                                                    415/200
7,442,444 B2    10/2008 Hazel et al.
(Continued)

OTHER PUBLICATIONS

U.S. Non-Final Office Action issued in connection with related U.S. Appl. No. 15/267,370 dated Mar. 1, 2017.
(Continued)

*Primary Examiner* — Jonathan C Langman
(74) *Attorney, Agent, or Firm* — General Electric Company; William Andes

(57) ABSTRACT

A ceramic component is generally provided that includes a silicon-based layer comprising a silicon-containing material (e.g., a silicon metal and/or a silicide) and about 0.001% to about 85% of a Ga-containing compound. For example, the silicon-based layer can be a bond coating directly on the surface of the substrate. Alternatively or additionally, the silicon-based layer can be an outer layer defining a surface of the substrate, with an environmental barrier coating on the surface of the substrate. Gas turbine engines are also generally provided that include such a ceramic component.

20 Claims, 3 Drawing Sheets

(51) Int. Cl.
*C04B 35/565* (2006.01)
*C04B 35/58* (2006.01)
*C01G 15/00* (2006.01)
*C30B 29/40* (2006.01)

(56) References Cited

U.S. PATENT DOCUMENTS

| | | | |
|---|---|---|---|
| 8,658,291 B2 | 2/2014 | Kirby et al. | |
| 2004/0237713 A1* | 12/2004 | Breslin | C04B 35/5611 75/235 |
| 2010/0080984 A1* | 4/2010 | Lee | C04B 35/16 428/334 |
| 2010/0154422 A1 | 6/2010 | Kirby et al. | |
| 2010/0159261 A1* | 6/2010 | Kirby | C04B 41/009 428/471 |
| 2010/0255260 A1* | 10/2010 | Lee | C23C 26/00 428/164 |
| 2011/0027557 A1* | 2/2011 | Kirby | C04B 41/009 428/215 |
| 2011/0027559 A1 | 2/2011 | Kirby et al. | |
| 2013/0167374 A1 | 7/2013 | Kirby et al. | |
| 2013/0177440 A1 | 7/2013 | Zhang et al. | |
| 2013/0177441 A1 | 7/2013 | Das et al. | |
| 2014/0050929 A1 | 2/2014 | Das | |
| 2014/0050930 A1 | 2/2014 | Das et al. | |
| 2014/0342168 A1 | 11/2014 | Lipkin | |
| 2016/0312628 A1 | 10/2016 | Kirby | |

OTHER PUBLICATIONS

GE Related Case Form.
International Search Report and Written Opinion issued in connection with corresponding PCT Application No. PCT/US2017/049849 dated Nov. 2, 2017.
Kirby, G. H., et al., "Silicon-based materials containing indium and methods of forming the same," GE co-pending U.S. Appl. No. 15/267,370, filed Sep. 16, 2016.
Kirby, G. H., et al., "Silicon composition containing gallium, indium, or a mixture thereof," GE co-pending U.S. Appl. No. 15/267,400, filed Sep. 16, 2016.

* cited by examiner

US 10,138,740 B2

SILICON-BASED MATERIALS CONTAINING GALLIUM AND METHODS OF FORMING THE SAME

FIELD OF THE INFORMATION

The present invention generally relates to including gallium (Ga) compounds within a silicon based coating. In particular, silicon-based coatings (e.g., silicon bond coatings) that include Ga are generally provided for use in environmental barrier coatings for ceramic components.

BACKGROUND OF THE INVENTION

Higher operating temperatures for gas turbine engines are continuously being sought in order to improve their efficiency. However, as operating temperatures increase, the high temperature durability of the components of the engine must correspondingly increase. Significant advances in high temperature capabilities have been achieved through the formulation of iron, nickel, and cobalt-based superalloys. Still, with many hot gas path components constructed from super alloys, thermal barrier coatings (TBCs) can be utilized to insulate the components and can sustain an appreciable temperature difference between the load-bearing alloys and the coating surface, thus limiting the thermal exposure of the structural component.

While superalloys have found wide use for components used throughout gas turbine engines, and especially in the higher temperature sections, alternative lighter-weight substrate materials have been proposed, such as ceramic matrix composite (CMC) materials. CMC and monolithic ceramic components can be coated with environmental barrier coatings (EBCs) to protect them from the harsh environment of high temperature engine sections. EBCs can provide a dense, hermetic seal against the corrosive gases in the hot combustion environment.

Silicon carbide and silicon nitride ceramics undergo oxidation in dry, high temperature environments. This oxidation produces a passive, silicon oxide scale on the surface of the material. In moist, high temperature environments containing water vapor, such as a turbine engine, both oxidation and recession occurs due to the formation of a passive silicon oxide scale and subsequent conversion of the silicon oxide to gaseous silicon hydroxide. To prevent recession in moist, high temperature environments, environmental barrier coatings (EBC's) are deposited onto silicon carbide and silicon nitride materials.

Currently, EBC materials are made out of rare earth silicate compounds. These materials seal out water vapor, preventing it from reaching the silicon oxide scale on the silicon carbide or silicon nitride surface, thereby preventing recession. Such materials cannot prevent oxygen penetration, however, which results in oxidation of the underlying substrate. Oxidation of the substrate yields a passive silicon oxide scale, along with the release of carbonaceous or nitrous oxide gas. The carbonaceous (i.e., CO, $CO_2$) or nitrous (i.e., NO, $NO_2$, etc.) oxide gases cannot escape out through the dense EBC and thus, blisters form. The use of a silicon bond coat has been the solution to this blistering problem to date. The silicon bond coat provides a layer that oxidizes (forming a passive silicon oxide layer beneath the EBC) without liberating a gaseous by-product.

However, the presence of a silicon bond coat limits the upper temperature of operation for the EBC because the melting point of silicon metal is relatively low. In use, a thermally grown oxide (TGO) layer of silicon oxide forms on the top surface of the silicon metal bond coat of a multilayer EBC system. This silicon oxide scale remains amorphous at temperatures of 1200° C. or lower, sometimes even at temperatures of 1315° C. or lower, although this property is also dependent on the time the bond coat is exposed to this temperature. At higher temperatures, or when minor amounts of steam penetrate through the EBC to the bond coat, the silicon oxide scale crystallizes (e.g., into cristoblate), which undergoes phase transition accompanied by large volume change on cooling. The volume change leads to EBC coating spall.

As such, it is desirable to improve the properties of a silicon bond coat in the EBC to achieve a higher operational temperature limit for the EBC.

BRIEF DESCRIPTION OF THE INVENTION

Aspects and advantages of the invention will be set forth in part in the following description, or may be obvious from the description, or may be learned through practice of the invention.

A ceramic component is generally provided that includes a silicon-based layer comprising a silicon-containing material (e.g., a silicon metal and/or a silicide) and about 0.001% to about 85% of a Ga-containing compound. For example, the silicon-based layer can be a bond coating directly on the surface of the substrate. Alternatively or additionally, the silicon-based layer can be an outer layer defining a surface of the substrate, with an environmental barrier coating on the surface of the substrate. Gas turbine engines are also generally provided that include such a ceramic component.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended Figs., in which.

Figure 1:
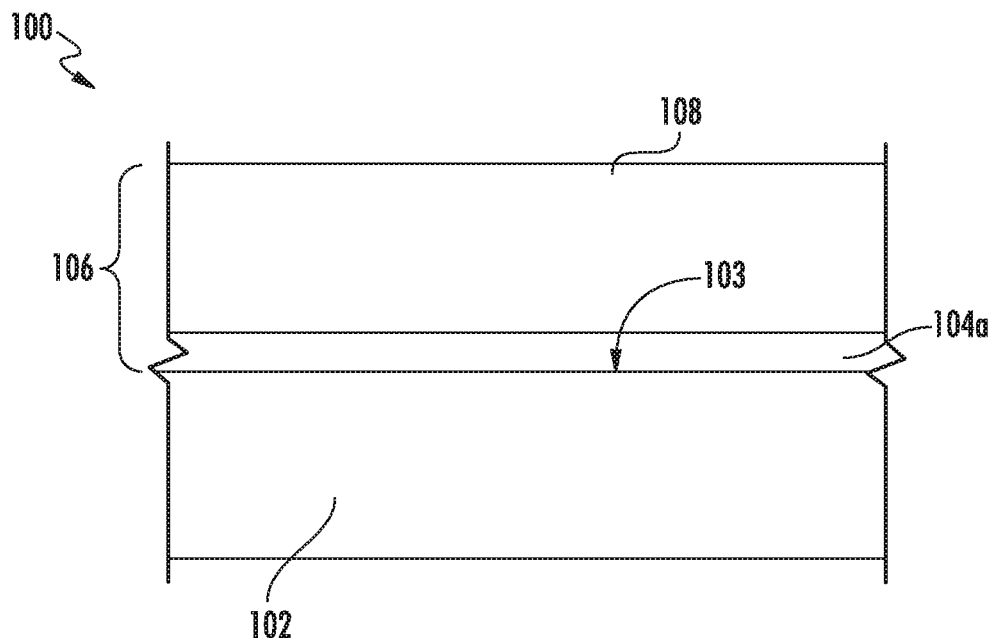
FIG. 1 is a cross-sectional side view of an exemplary ceramic component including a silicon-based layer.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth. As used herein, "Ln" refers to a rare earth element or a mixture of rare earth elements. More specifically, the "Ln" refers to the rare earth elements of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), or mixtures thereof.

In the present disclosure, when a layer is being described as "on" or "over" another layer or substrate, it is to be understood that the layers can either be directly contacting each other or have another layer or feature between the layers, unless expressly stated to the contrary. Thus, these terms are simply describing the relative position of the layers to each other and do not necessarily mean "on top of" since the relative position above or below depends upon the orientation of the device to the viewer.

Silicon-based coatings that include Ga are generally provided for use with environmental barrier coatings for ceramic components, along with their methods of formation. In particular embodiments, silicon-based bond coatings for environmental barrier coatings (EBCs) are generally provided for high temperature ceramic components, along with methods of its formation and use. In particular, the silicon-based bond coating includes a component containing Ga for preventing crystallization of a thermal growth oxide ("TGO") on silicon-based bond coating in an EBC, which in turn prevents spall of the coating caused by such crystallization of the TGO. That is, the introduction of Ga within the silicon-based bond coating keeps the TGO (i.e., the SiO) in an amorphous phase. Accordingly, the operating temperature of the silicon-based bond coating (and thus the TGO and EBC coating) can be increased. Additionally, the inclusion of Ga can inhibit and prevent crystallization of the TGO without greatly accelerating the growth rate of the TGO. Additionally, Ga-containing components have limited reaction with and/or solubility into in silicon oxide, which can limit the rate of oxide scale growth.

FIGS. 1-4 show exemplary embodiments of a ceramic component 100 formed from a substrate 102 and a silicon-based layer 104a (FIG. 1), 104b (FIG. 3), respectively. Each of the silicon-based layers 104a, 104b includes a silicon-containing material and about 0.001% to about 85% by a Ga-containing compound, such as about 1% to about 60% by weight of a Ga-containing compound (e.g., about 1% to about 50% by weight, such as about 1% to about 25% by weight). Generally, the Ga-containing compound is unreactive with the composition of the silicon-based layer 104a (e.g., silicon metal).

In one embodiment, the silicon-based layer 104a may include the Ga-containing compound and a silicon-containing material (e.g., silicon metal, a silicide, etc.) in continuous phases that are intertwined with each other. For example, the silicon-containing material and the Ga-containing compound are intertwined continuous phases having about 0.001% to about 85% by volume of the Ga-containing compound, such as about 1% to about 60% by volume (e.g., about 40% to about 60% by volume of the Ga-containing compound). For example, the silicon-based layer 104a can include the Ga-containing compound in about 15% by volume to about 85% by volume, with the balance being the silicon containing compound.

In another embodiment, the Ga-containing compound forms a plurality of discrete phases dispersed within the silicon-containing material (e.g., within a continuous phase of the silicon-containing material), such as discrete particulate phases. In such an embodiment, the silicon-based layer 104a can include about 0.001% to about 40% by volume of the Ga-containing compound, such as about 1% to about 25% by volume (e.g., about 1% to about 10% by volume of the Ga-containing compound).

In one particular embodiment, the substrate 102 is formed from a CMC material (e.g., a silicon based, non-oxide ceramic matrix composite). As used herein, "CMCs" refers to silicon-containing, or oxide-oxide, matrix and reinforcing materials. As used herein, "monolithic ceramics" refers to materials without fiber reinforcement (e.g., having the matrix material only). Herein, CMCs and monolithic ceramics are collectively referred to as "ceramics."

Some examples of CMCs acceptable for use herein can include, but are not limited to, materials having a matrix and reinforcing fibers comprising non-oxide silicon-based materials such as silicon carbide, silicon nitride, silicon oxycarbides, silicon oxynitrides, and mixtures thereof. Examples include, but are not limited to, CMCs with silicon carbide matrix and silicon carbide fiber; silicon nitride matrix and silicon carbide fiber; and silicon carbide/silicon nitride matrix mixture and silicon carbide fiber. Furthermore, CMCs can have a matrix and reinforcing fibers comprised of oxide ceramics. Specifically, the oxide-oxide CMCs may be comprised of a matrix and reinforcing fibers comprising oxide-based materials such as aluminum oxide ($Al_2O_3$), silicon dioxide ($SiO_2$), aluminosilicates, and mixtures thereof. Aluminosilicates can include crystalline materials such as mullite ($3Al_2O_3 \cdot 2SiO_2$), as well as glassy aluminosilicates.

In the embodiment of FIG. 1, the substrate 102 defines a surface 103 having a coating 106 formed thereon. The coating 106 includes the silicon-based layer 104a and an environmental barrier coating 108. In one particular embodiment, the silicon-based layer 104a is a bond coating, where the silicon containing material is silicon metal, a silicide (e.g., a rare earth silicide, a molybdenum silicide, a rhenium silicide, or mixtures thereof), or a mixture thereof. In one embodiment, a composition is generally provided that includes silicon metal and the Ga-containing compound, such as in the relative amounts described above (e.g., about 0.01 to about 85% by volume). In an alternative embodiment, a composition is generally provided that includes a silicide (e.g., a rare earth silicide, a molybdenum silicide, a rhenium silicide, or mixtures thereof) and the Ga-containing compound, such as in the relative amounts described above (e.g., about 0.01 to about 85% by volume).

Figure 2:
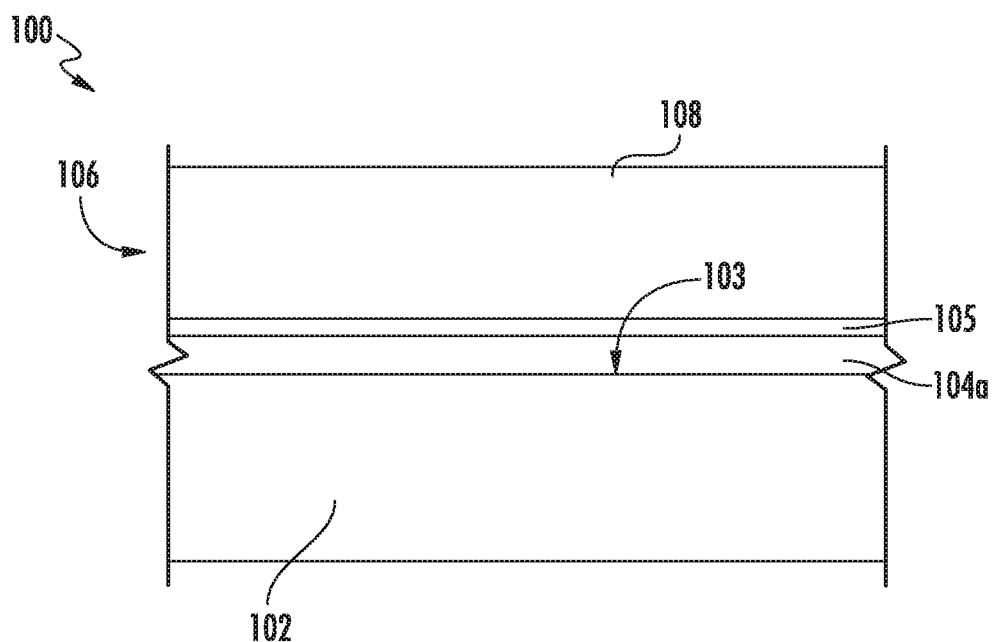
FIG. 2 is a cross-sectional side view of the exemplary ceramic component of FIG. 1 including a thermally grown oxide layer on the silicon-based layer.

During use, a thermally grown oxide ("TGO") layer forms on the surface of the bond coating. For example, a layer of silicon oxide (sometimes referred to as "silicon oxide scale" or "silica scale") forms on a bond coating of silicon metal and/or a silicide. Referring to FIG. 2, a thermally grown oxide layer 105 (e.g., silicon oxide) is shown directly on the silicon-based layer 104a (e.g., a bond coating with the silicon containing material being silicon metal and/or a silicide), as forms during exposure to oxygen (e.g., during manufacturing and/or use) of the component 100. Due to the presence of the Ga-containing compound within the silicon-based layer 104a, the thermally grown oxide layer 105 remains substantially amorphous at its operating temperature, with the "operating temperature" referring to the temperature of the thermally grown oxide layer 105. For example, for silicon metal bond coatings, the TGO layer may remain amorphous at operating temperatures of about 1415° C. or less (e.g., about 1200° C. to about 1410° C.), which is just below the melting point of the silicon-based bond coating (Si metal has a melting point of about 1414° C.). In another example, for silicide bond coatings, the TGO layer may remain amorphous at operating temperatures of about 1485° C. or less (e.g., about 1200° C. to about 1415° C.), which is just below the maximum use temperature of the CMC. Without wishing to be bound by any particular theory, it is believed that gallium in the silicon-based layer 104a migrates into the thermally grown oxide layer 105 and inhibits crystallization of the thermally grown oxide layer (e.g., silicon oxide) that would otherwise occur at these temperatures. Without wishing to be bound by any particular theory, it is presently believed that Ga inhibits impurities such as Na and/or K from causing crystallization of the amorphous silicon-containing material.

In the embodiment shown in FIGS. 1 and 2, the silicon-based layer 104a is directly on the surface 103 without any layer therebetween. However, in other embodiments, one or more layers can be positioned between the silicon-based layer 104a and the surface 103.

Figure 3:
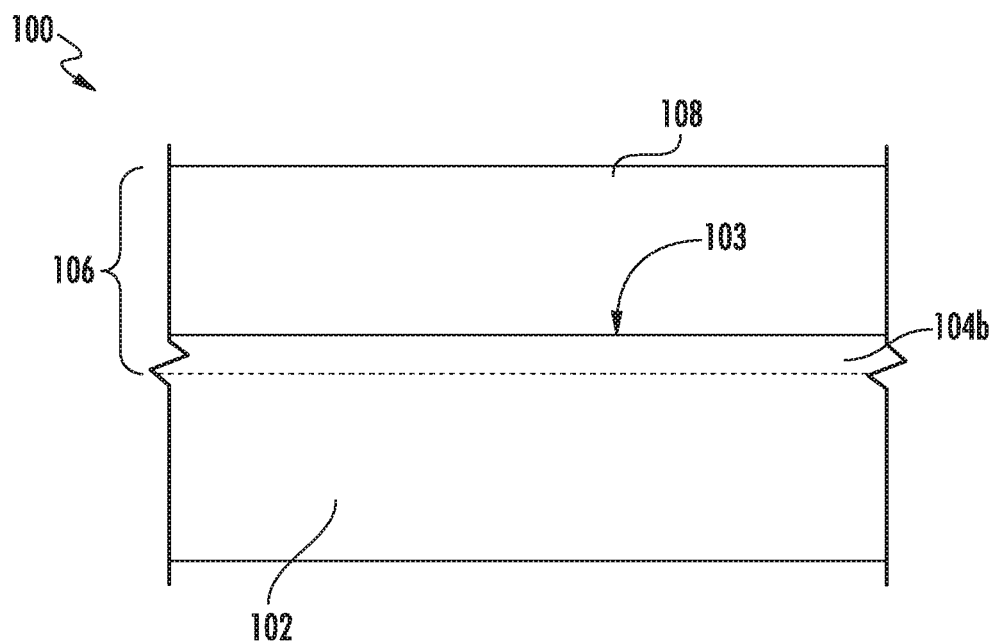
FIG. 3 is a cross-sectional side view of another exemplary ceramic component including a silicon-based layer.

FIG. 3 shows another embodiment of a ceramic component 100 with the substrate 102 having an outer layer 104b that defines a surface 103 of the substrate 102. That is, the outer layer 104b is integral with the substrate 102. In this embodiment, the outer layer 104b is the silicon-based layer, and a coating 106 is on the surface 105. The coating 106 may include an environmental barrier coating 108 and/or other layers (e.g., a bond coating, etc.). In one embodiment, the outer layer 104b can be a silicon-containing monolithic ceramic layer. For example, the outer layer 104b may include silicon carbide. In one embodiment, the substrate 102 may include the outer layer 104b (e.g., including silicon carbide as a monolithic ceramic layer) on a plurality of CMC plies forming the remaining portion of the substrate.

Figure 4:
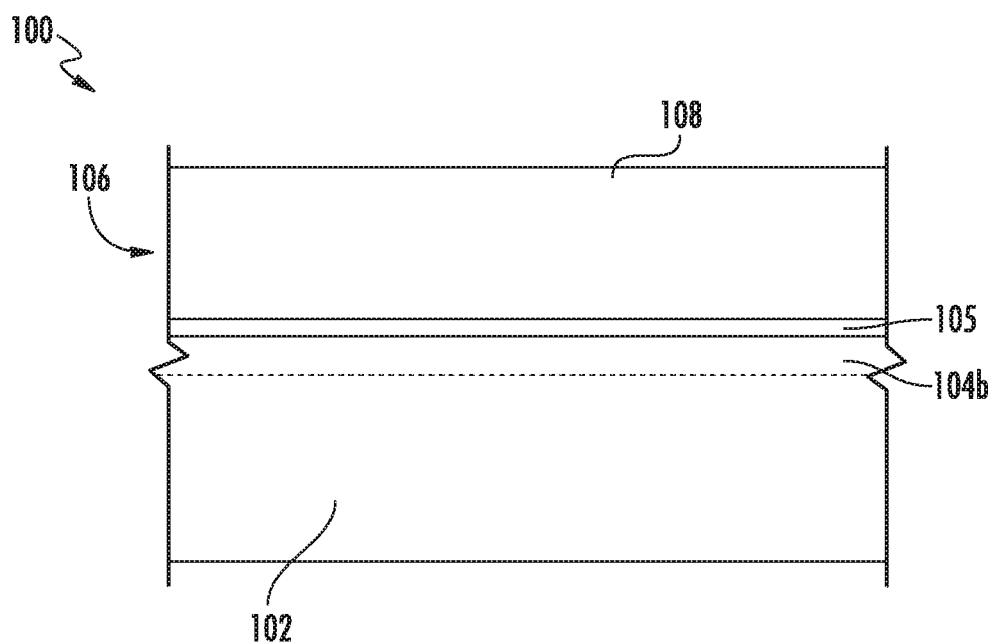
FIG. 4 is a cross-sectional side view of the exemplary ceramic component of FIG. 3 including a thermally grown oxide layer on the silicon-based layer.

FIG. 4 shows a thermally grown oxide layer 105 (e.g., silicon oxide) directly on the silicon-based layer 104b (e.g., a bond coating with the silicon containing material being silicon metal), as forms during exposure to oxygen (e.g., during manufacturing and/or use) of the component 100. Due to the presence of the Ga-containing compound within the silicon-based layer 104b, the thermally grown oxide layer 105 remains substantially amorphous at the operating temperature of the thermally grown oxide layer 105. Without wishing to be bound by any particular theory, it is believed that gallium in the silicon-based layer 104b migrates into the thermally grown oxide layer 105 and inhibits crystallization of the thermally grown oxide layer (e.g., silicon oxide) that would otherwise occur at these temperatures.

As stated, a Ga-containing compound is included within the silicon-based layer 104a, 104b, no matter the particular positioning of the silicon-based layer 104 in the ceramic component 100. In particular embodiments, the Ga-containing compound is in the form of an oxide or a nitride. For example, the Ga-containing compound can be gallium nitride (GaN), gallium oxide ($Ga_2O_3$), or a mixture thereof. In the embodiment where the Ga-containing compound includes gallium oxide, the gallium oxide can be doped within another oxide. For example, the Ga-containing compound can be zirconium oxide ($ZrO_2$), hafnium oxide ($HfO_2$), or a combination thereof doped with up to about 10 mole % of $Ga_2O_3$.

In one embodiment, the Ga-containing compound can be a gallium-metal-oxide. For example, the Ga-containing compound can have, in one embodiment, a formula of:

$$Ga_{2-x}M_xO_3$$

where M is In with x being 0 to less than 2, Al with x being 0 to about 1.4, B with x being 0 to about 1.4, Fe with x being 0 to about 1.4, or a mixture thereof. In one embodiment, M is In with x being greater than 0 to less than 2, Al with x being greater than 0 to about 1.4, B with x being greater than 0 to about 1.4, Fe with x being greater than 0 to about 1.4, or a mixture thereof, such that at least one other metal (In, Al, B, and/or Fe) is present in the gallium-metal-oxide.

In one embodiment, the Ga-containing compound can be a rare earth-gallium-oxide. For example, the Ga-containing compound can have, in one embodiment, a formula of:

$$Ln_{4-x}D_xGa_{2-y}In_yO_9$$

where Ln is La, Ce, Pr, Nd, Pm, Sm, or a mixture thereof; D is La, Ce, Pr, Nd, Pm, Sm, Eu, Gd, Tb, Dy, Ho, Er, Tm, Yb, Lu, or a mixture thereof, with D being different than Ln (i.e., D is a different element or combination of elements than Ln); and y is 0 to about 1 (e.g., $0 \leq y \leq 1$, such as $0 \leq y \leq 0.5$). In one particular embodiment, y is greater than 0 to about 1 (e.g., $0 < y \leq 1$, such as $0 < y \leq 0.5$). If D is La, Ce, Pr, Nd, Pm, Sm, or a mixture thereof (i.e., having an atomic radius of Sm or larger), then x is 0 to less than 4 (e.g., $0 < x < 4$, such as $0 < x \leq$ about 2). However, if D is Eu, Gd, Tb, Dy, Ho, Er, Tm, Yb, Lu, or a mixture thereof (i.e., having an atomic radius that is smaller than Sm), then x is 0 to about 2 (e.g., $0 < x < 2$, such as $0 < x \leq$ about 1).

In another embodiment, the Ga-containing compound can have a formula of:

$$Ln_3Ga_{5-x}M_xO_{12}$$

where Ln is Sc, Y, La, Ce, Pr, Nd, Pm, Sm, Eu, Gd, Tb, Dy, Ho, Er, Tm, Yb, Lu, or a mixture thereof; and M is In with x being 0 to less than 5 (e.g., $0 \leq x < 5$, such as $0 < x \leq 2.5$), Al with x being 0 to less than 5 (e.g., $0 \leq x < 5$, such as $0 < x \leq 2.5$), Fe with x being 0 to less than 5 (e.g., $0 \leq x < 5$, such as $0 < x \leq 2.5$), B with x being 0 to about 2.5 (e.g., $0 \leq x \leq 2.5$), or a combination thereof. In one particular embodiment, M is B, with x being greater than 0 to about 2.5 (e.g., $0 < x \leq 2.5$), such as about 0.1 to about 2 (e.g., $0.1 \leq x \leq 2$). In one embodiment, x is greater than 0 (e.g., 0.1 to about 2) such that at least one of M (e.g., In, Al, Fe, and/or B) is present in the Ga-containing compound.

In one embodiment, the Ga-containing compound can have a formula of:

$$Ln_{2-x-y}Ga_xIn_ySi_2O_7$$

where Ln is Sc, Y, La, Ce, Pr, Nd, Pm, Sm, Eu, Gd, Tb, Dy, Ho, Er, Tm, Yb, Lu, or a mixture thereof; x is greater than 0 to about 1; and y is 0 to about 1. In one embodiment, the sum of x and y is greater than 0 up to about 1 (i.e., 0<(x+y)≤about 1), such as about greater than 0 up to about 0.5 (i.e., 0<(x+y)≤about 0.5). In one embodiment, y is 0.

In one embodiment, the Ga-containing compound can have a formula of:

$$Ln_{2-x-y}Ga_xIn_ySi_2O_5$$

where Ln is Sc, Y, La, Ce, Pr, Nd, Pm, Sm, Eu, Gd, Tb, Dy, Ho, Er, Tm, Yb, Lu, or a mixture thereof; x is greater than 0 to about 1; and y is 0 to about 1. In one embodiment, the sum of x and y is greater than 0 up to about 1 (i.e., 0<(x+y)≤about 1), such as about greater than 0 up to about 0.5 (i.e., 0<(x+y)≤about 0.5). In one embodiment, y is 0.

The environmental barrier coating 108 of FIGS. 1-4 can include any combination of one or more layers formed from materials selected from typical EBC or TBC layer chemistries, including but not limited to rare earth silicates (mono- and di-silicates), mullite, barium strontium aluminosilicate (BSAS), hafnia, zirconia, stabilized hafnia, stabilized zirconia, rare earth hafnates, rare earth zirconates, rare earth gallates, etc.

The ceramic component 100 of FIGS. 1-4 is particularly suitable for use as a component found in high temperature environments, such as those present in gas turbine engines, for example, combustor components, turbine blades, shrouds, nozzles, heat shields, and vanes. In particular, the turbine component can be a CMC component positioned within a hot gas flow path of the gas turbine such that the coating forms an environmental barrier coating on the component to protect the component within the gas turbine when exposed to the hot gas flow path.

Figure 5:
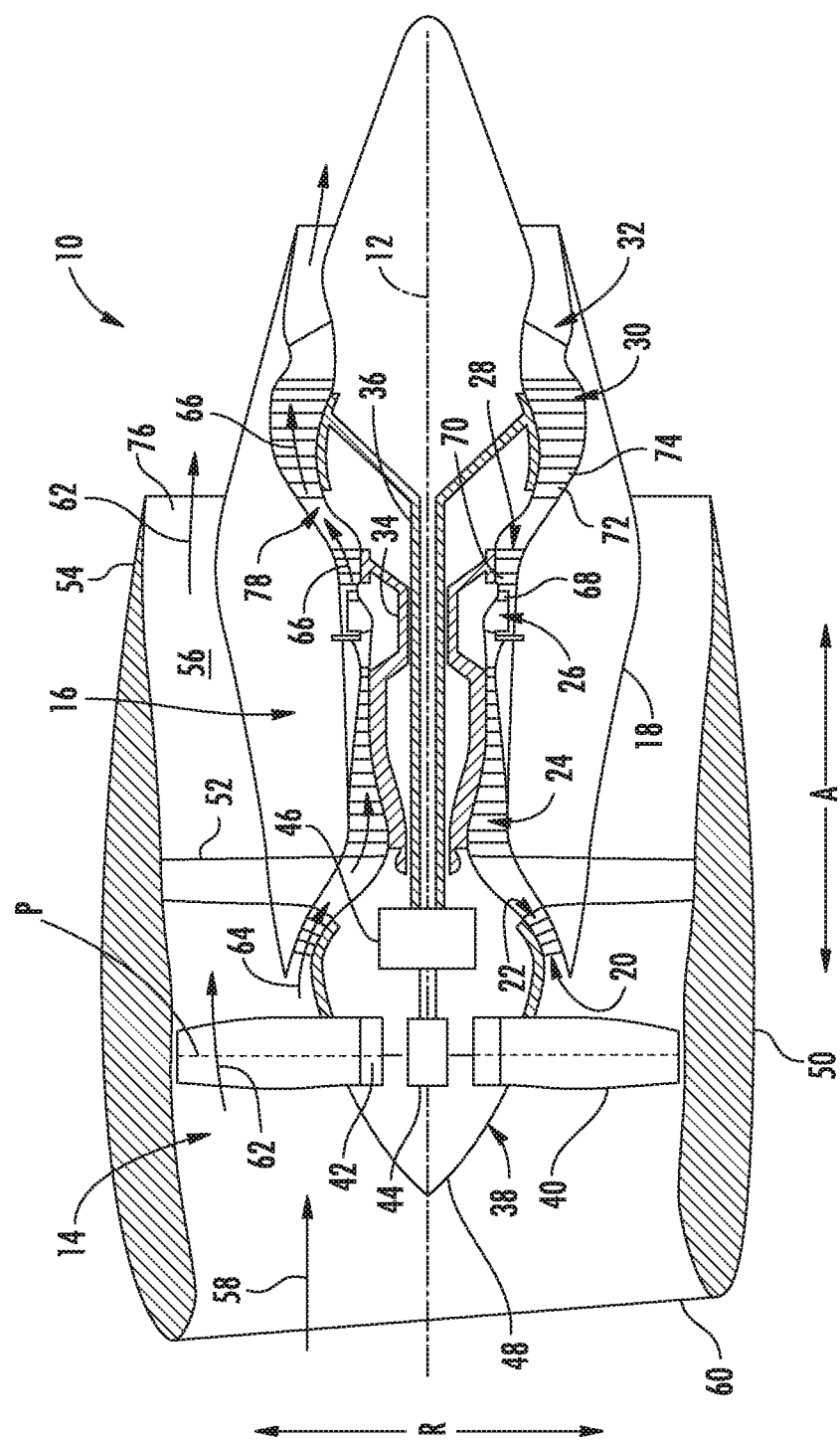
FIG. 5 is a schematic cross-sectional view of an exemplary gas turbine engine according to various embodiments of the present subject matter.

FIG. 5 is a schematic cross-sectional view of a gas turbine engine in accordance with an exemplary embodiment of the present disclosure. More particularly, for the embodiment of FIG. 5, the gas turbine engine is a high-bypass turbofan jet engine 10, referred to herein as "turbofan engine 10." As shown in FIG. 5, the turbofan engine 10 defines an axial direction A (extending parallel to a longitudinal centerline 12 provided for reference) and a radial direction R. In general, the turbofan 10 includes a fan section 14 and a core turbine engine 16 disposed downstream from the fan section 14. Although described below with reference to a turbofan engine 10, the present disclosure is applicable to turbomachinery in general, including turbojet, turboprop and turboshaft gas turbine engines, including industrial and marine gas turbine engines and auxiliary power units.

The exemplary core turbine engine 16 depicted generally includes a substantially tubular outer casing 18 that defines an annular inlet 20. The outer casing 18 encases, in serial flow relationship, a compressor section including a booster or low pressure (LP) compressor 22 and a high pressure (HP) compressor 24; a combustion section 26; a turbine section including a high pressure (HP) turbine 28 and a low pressure (LP) turbine 30; and a jet exhaust nozzle section 32. A high pressure (HP) shaft or spool 34 drivingly connects the HP turbine 28 to the HP compressor 24. A low pressure (LP) shaft or spool 36 drivingly connects the LP turbine 30 to the LP compressor 22.

For the embodiment depicted, the fan section 14 includes a variable pitch fan 38 having a plurality of fan blades 40 coupled to a disk 42 in a spaced apart manner. As depicted, the fan blades 40 extend outwardly from disk 42 generally along the radial direction R. Each fan blade 40 is rotatable relative to the disk 42 about a pitch axis P by virtue of the fan blades 40 being operatively coupled to a suitable actuation member 44 configured to collectively vary the pitch of the fan blades 40 in unison. The fan blades 40, disk 42, and actuation member 44 are together rotatable about the longitudinal axis 12 by LP shaft 36 across an optional power gear box 46. The power gear box 46 includes a plurality of gears for stepping down the rotational speed of the LP shaft 36 to a more efficient rotational fan speed.

Referring still to the exemplary embodiment of FIG. 5, the disk 42 is covered by rotatable front nacelle 48 aerodynamically contoured to promote an airflow through the plurality of fan blades 40. Additionally, the exemplary fan section 14 includes an annular fan casing or outer nacelle 50 that circumferentially surrounds the fan 38 and/or at least a portion of the core turbine engine 16. It should be appreciated that the nacelle 50 may be configured to be supported relative to the core turbine engine 16 by a plurality of circumferentially-spaced outlet guide vanes 52. Moreover, a downstream section 54 of the nacelle 50 may extend over an outer portion of the core turbine engine 16 so as to define a bypass airflow passage 56 therebetween.

During operation of the turbofan engine 10, a volume of air 58 enters the turbofan 10 through an associated inlet 60 of the nacelle 50 and/or fan section 14. As the volume of air 58 passes across the fan blades 40, a first portion of the air 58 as indicated by arrows 62 is directed or routed into the bypass airflow passage 56 and a second portion of the air 58 as indicated by arrow 64 is directed or routed into the LP compressor 22. The ratio between the first portion of air 62 and the second portion of air 64 is commonly known as a bypass ratio. The pressure of the second portion of air 64 is then increased as it is routed through the high pressure (HP) compressor 24 and into the combustion section 26, where it is mixed with fuel and burned to provide combustion gases 66.

The combustion gases 66 are routed through the HP turbine 28 where a portion of thermal and/or kinetic energy from the combustion gases 66 is extracted via sequential stages of HP turbine stator vanes 68 that are coupled to the outer casing 18 and HP turbine rotor blades 70 that are coupled to the HP shaft or spool 34, thus causing the HP shaft or spool 34 to rotate, thereby supporting operation of the HP compressor 24. The combustion gases 66 are then routed through the LP turbine 30 where a second portion of thermal and kinetic energy is extracted from the combustion gases 66 via sequential stages of LP turbine stator vanes 72 that are coupled to the outer casing 18 and LP turbine rotor blades 74 that are coupled to the LP shaft or spool 36, thus causing the LP shaft or spool 36 to rotate, thereby supporting operation of the LP compressor 22 and/or rotation of the fan 38.

The combustion gases 66 are subsequently routed through the jet exhaust nozzle section 32 of the core turbine engine 16 to provide propulsive thrust. Simultaneously, the pressure of the first portion of air 62 is substantially increased as the first portion of air 62 is routed through the bypass airflow passage 56 before it is exhausted from a fan nozzle exhaust section 76 of the turbofan 10, also providing propulsive thrust. The HP turbine 28, the LP turbine 30, and the jet exhaust nozzle section 32 at least partially define a hot gas path 78 for routing the combustion gases 66 through the core turbine engine 16.

Methods are also generally provided for coating a ceramic component. In one embodiment, the method includes applying a bond coating directly on a surface of the ceramic component, where the bond coating comprises a silicon-containing material (e.g., silicon metal and/or a silicide) and a Ga-containing compound, such as described above.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A ceramic component comprising: a substrate defining a surface; and a silicon-based layer forming a bond coating directly on the surface of the substrate, wherein the silicon-based layer comprises a silicon-containing material and about 1% to 25% by weight of a Ga-containing compound, wherein the substrate is formed from a ceramic matrix composite (CMC) material, and wherein the silicon-containing material forms a continuous phase within the silicon-based layer.

2. The ceramic component as in claim 1, wherein the silicon-containing material is silicon metal.

3. The ceramic component as in claim 2, wherein a thermally grown oxide is on the bond coating, and wherein the thermally grown oxide layer remains amorphous up to an operating temperature of about 1415° C. or less.

4. The ceramic component as in claim 1, wherein the silicon-containing material comprises a silicide.

5. The ceramic component as in claim 4, wherein a thermally grown oxide is on the bond coating, and wherein the thermally grown oxide layer remains amorphous up to an operating temperature of about 1485° C. or less.

6. The ceramic component as in claim 4, wherein the silicide comprises molybdenum silicide, rhenium silicide, or a mixture thereof.

7. The ceramic component as in claim 1, wherein the silicon-based layer is an outer layer on the surface of the substrate; and the ceramic component further includes
    an environmental barrier coating on the silicon-based layer.

8. The ceramic component as in claim 7, wherein the substrate comprises the outer layer on a plurality of CMC plies, and wherein the outer layer comprises silicon carbide.

9. The ceramic component as in claim 1, wherein the Ga-containing compound comprises $Ga_{2-x}M_xO_3$ where M is In with x being 0 to about 2, Al with x being 0 to about 1.4, B with x being 0 to about 1.4, Fe with x being 0 to about 1.4, or a mixture thereof.

10. The ceramic component as in claim 1, wherein the Ga-containing compound comprises $ZrO_2$, $HfO_2$, or a combination thereof doped with about 0.1% to about 10% by mole percent of $Ga_2O_3$.

11. The ceramic component as in claim 1, wherein the Ga-containing compound comprises a compound having a formula:

$$Ln_{4-x}D_xGa_{2-y}In_yO_9$$

where:
Ln is La, Ce, Pr, Nd, Pm, Sm, or a mixture thereof;
D is La, Ce, Pr, Nd, Pm, Sm, Eu, Gd, Tb, Dy, Ho, Er, Tm, Yb, Lu, or a mixture thereof, where:
    D is not equal to Ln;
    if D is La, Ce, Pr, Nd, Pm, Sm, or a mixture thereof, then x is 0 to less than 4;
    if D is Eu, Gd, Tb, Dy, Ho, Er, Tm, Yb, Lu, or a mixture thereof, then
    x is 0 to about 2; and y is 0 to about 1.

12. The ceramic component as in claim 1, wherein the Ga-containing compound comprises a compound having a formula:

$$Ln_{2-x-y}Ga_xIn_ySi_2O_7$$

where
Ln is Sc, Y, La, Ce, Pr, Nd, Pm, Sm, Eu, Gd, Tb, Dy, Ho, Er, Tm, Yb, Lu, or a mixture thereof;
x is greater than 0 to about 1; and
y is 0 to about 1.

13. The ceramic component as in claim 1, wherein the Ga-containing compound comprises a compound having a formula:

$$Ln_{2-x-y}Ga_xIn_ySi_2O_5$$

where
Ln is Sc, Y, La, Ce, Pr, Nd, Pm, Sm, Eu, Gd, Tb, Dy, Ho, Er, Tm, Yb, Lu, or a mixture thereof;
x is greater than 0 to about 1; and
y is 0 to about 1.

14. The ceramic component as in claim 1, wherein the Ga-containing compound comprises a compound having a formula:

$$Ln_3Ga_{5-x}M_xO_{12}$$

where
Ln is Sc, Y, La, Ce, Pr, Nd, Pm, Sm, Eu, Gd, Tb, Dy, Ho, Er, Tm, Yb, Lu, or a mixture thereof; and
M is In with 0≤x<5, Al with 0≤x<5, Fe with 0≤x<5, B with 0≤x≤2.5, or a combination thereof.

15. The ceramic component as in claim 1, wherein the Ga-containing compound comprises GaN.

16. The ceramic component as in claim 1, wherein the Ga-containing compound is selected from the group consisting of:
    GaN;
    $Ga_2O_3$;
    $Ga_{2-x}M_xO_3$ where M is In with x being 0 to about 2, Al with x being 0 to about 1.4, B with x being 0 to about 1.4, Fe with x being 0 to about 1.4, or a mixture thereof;
    $ZrO_2$, $HfO_2$, or a combination thereof doped with up to about 10 mole % of $Ga_2O_3$;
    $Ln_{4-x}D_xGa_{2-y}In_yO_9$, where: Ln is La, Ce, Pr, Nd, Pm, Sm, or a mixture thereof; D is La, Ce, Pr, Nd, Pm, Sm, Eu, Gd, Tb, Dy, Ho, Er, Tm, Yb, Lu, or a mixture thereof, where D is not equal to Ln, if D is La, Ce, Pr, Nd, Pm, Sm, or a mixture thereof, then x is 0 to less than 4, if D is Eu, Gd, Tb, Dy, Ho, Er, Tm, Yb, Lu, or a mixture thereof, then x is 0 to about 2; and y is 0 to about 1;
    $Ln_3Ga_{5-x}M_{12}$, where Ln is Sc, Y, La, Ce, Pr, Nd, Pm, Sm, Eu, Gd, Tb, Dy, Ho, Er, Tm, Yb, Lu, or a mixture thereof; and M is In with 0 ≤x <5, Al with 0 ≤x <5, Fe with 0 ≤x <5, B with 0 ≤x ≤2.5, or a combination thereof; and
    a mixture thereof.

17. A gas turbine engine comprising the ceramic component of claim 1.

18. The ceramic component as in claim 1, wherein the silicon-based layer comprises the Ga-containing compound and the silicon-containing material in continuous phases that are intertwined with each other.

19. The ceramic component as in claim 1, wherein the silicon-based layer comprises a plurality of discrete phases of the Ga-containing compound dispersed within the continuous phase of the silicon-containing material.

20. The ceramic component as in claim 1, wherein the silicon-based layer consists of the silicon-containing material and about 1% to 25% by weight of the Ga-containing compound.

* * * * *